United States Patent [19]

Kellner

[11] Patent Number: 5,407,668
[45] Date of Patent: Apr. 18, 1995

[54] CLEAR DEODORANT STICK COMPOSITIONS

[75] Inventor: David M. Kellner, Hollis, N.Y.

[73] Assignee: Revlon Consumer Products Corporation, New York, N.Y.

[21] Appl. No.: 102,319

[22] Filed: Aug. 5, 1993

[51] Int. Cl.⁶ .......................... A61K 7/32; A61K 7/36
[52] U.S. Cl. ................................ 424/65; 424/DIG. 5; 424/67
[58] Field of Search ...................... 424/DIG. 5, 68, 67, 424/65

[56] References Cited

U.S. PATENT DOCUMENTS

| | | | |
|---|---|---|---|
| 2,819,995 | 1/1958 | Wassell | 424/DIG. 5 |
| 2,828,265 | 3/1958 | Van Shrien | 252/316 |
| 2,857,315 | 10/1958 | Teller | 424/66 |
| 4,120,948 | 10/1978 | Shelton | 424/66 |
| 4,226,889 | 10/1980 | Yuhas | 424/49 |
| 4,268,448 | 5/1981 | Gedeon | 424/66 |
| 4,504,465 | 3/1985 | Sampson | 424/65 |
| 4,617,185 | 10/1986 | Di Pietro | 424/65 |
| 4,702,916 | 10/1987 | Geria | 424/400 |
| 4,732,754 | 3/1988 | Krevald | 424/66 |
| 4,759,924 | 7/1988 | Luebbe | 424/42 |
| 4,816,261 | 3/1989 | Luebbe | 424/65 |
| 4,948,578 | 8/1990 | Burgen | 424/65 |
| 4,954,333 | 9/1990 | Wand | 424/66 |
| 5,120,541 | 6/1992 | Macaulay | 424/401 |
| 5,128,123 | 7/1992 | Bresten | 424/65 |

FOREIGN PATENT DOCUMENTS 92303976  11/1992  European Pat. Off. ........ A61K 7/48

Primary Examiner—Dale R. Ore
Attorney, Agent, or Firm—Julie Blackburn

[57] ABSTRACT

The invention is directed to a clear deodorant stick composition comprising:
1–20% soap,
0.01–10% of an antibacterial agent,
10–40% water,
40–90% polyhydric alcohol,
1–10% Pentadoxynol 200
1–20% of a clarity enhancing solubilizer which is a mixture (a) and (b) wherein:
(a) is an alkanolamide of the formula:

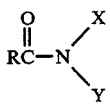

Wherein RCO is a fatty acid radical, X is $CHR_1CH_2OH$ wherein $R_1$ is H or lower alkyl; and Y is H, alkyl, alkanol, or $CHR_1CH_2OH$, and
(b) is an alkoxylated alcohol of the formula:

$$R_2(OCH_2CH_2)OH$$

wherein $R_2$ is H, $C_{4-22}$ straight or branched chain saturated or unsaturated alkyl, a phenyl ring substituted or unsubstituted with a $C_{4-22}$ straight or branched chain saturated or unsaturated alkyl, or

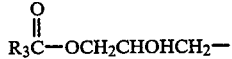

wherein $R_3$ is a C4–22 saturated or unsaturated alkyl.

14 Claims, No Drawings

CLEAR DEODORANT STICK COMPOSITIONS

TECHNICAL FIELD

The invention is in the field of deodorant compositions.

BACKGROUND OF THE INVENTION

Human perspiration is initially odorless but upon standing develops an unpleasant odor which is due almost entirely to bacterial decomposition of the perspiration. Cosmetic compositions designed to treat perspiration odor act either by inhibiting the flow of perspiration from the skin, or by eliminating only the odor associated with perspiration.

Antiperspirants inhibit perspiration flow because they contain metal salts which have astringent properties. Deodorants, on the other hand, do not alter the volume of perspiration secreted. Since most body odor is the result of bacterial action on perspiration, deodorants contain certain agents such as phenolic derivatives, quaternary ammonium compounds, hexachlorophene, and various ion exchange resins, all of which possess effective antibacterial action.

Today, many different types of deodorants are available. However, clear deodorant preparations are extremely popular because consumers associate clarity with cleanliness and effectiveness. It is particularly difficult to make clear deodorant sticks which have the stability required for commercial use. In many instances the clear stick products are tacky and long drying which causes the underarm to feel wet and sticky after the stick is applied. In addition, these sticks have poor stability, often will turn cloudy within days or months, which makes them unsuitable for commercial use.

Cosmetic compositions in stick form are well known. For example, U.S. Pat. No. 4,759,924 (Luebbe) discloses a transparent soap gel stick useful for deodorant purposes.

U.S. Pat. No. 4,816,261 also teaches clear deodorant sticks which contain the gelling agent dibenzylidene sorbitol monoacetal rather than soap.

U.S. Pat. No. 5,128,123 discloses a clear cosmetic stick which essentially contains an alkyoxylate copolymer.

U.S. Pat. No. 5,120,541 discloses transparent sticks containing monohydric alcohols and a soap crystal growth inhibitor.

U.S. Pat. No. 4,617,285 discloses a stick composition essentially containing diisopropyl adipate.

U.S. Pat. Nos. 4,504,465, 4,226,889, 4,702,916, and 4,732,754 also disclose cosmetic gel stick compositions containing soap.

None of the above references disclose the particular clear deodorant stick compositions of the invention.

The object of the invention is to develop a clear deodorant stick with improved clarity and stability.

Another object of the invention is to develop a clear deodorant stick which does not contain the benzylidene sorbitol gelling agents or monohydric alcohols.

SUMMARY OF THE INVENTION

The invention is directed to a clear deodorant stick composition comprising:
1–20% soap,
0.01–10% of an antibacterial agent,
10–40% water,
40–90% polyhydric alcohol,
1–10% Pentadoxynol 200
1–20% of a clarity enhancing solubilizer which is a mixture of (a) and (b) wherein:
(a) is an alkanolamide of the formula:

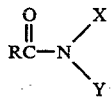

Wherein RCO is a fatty acid radical, X is $CHR_1CH_2OH$ wherein $R_1$ is H or lower alkyl; and Y is H, alkyl, alkanol, or $CHR_1CH_2OH$, and
(b) is an alkoxylated alcohol of the formula:

$$R_2(OCH_2CH_2)OH$$

wherein $R_2$ is H, $C_{4-22}$ straight or branched chain saturated or unsaturated alkyl, a phenyl ring substituted or unsubstituted with a $C_{4-22}$ straight or branched chain saturated or unsaturated alkyl, or

wherein $R_3$ is a $C_{4-22}$ saturated or unsaturated alkyl.

DETAILED DESCRIPTION

Fatty acids which form soap include behenic, capyric, isostearic, oleic, ricinoleate, myristic, palmitic, stearic, oleic, linoleic, margaric, or mixtures of these acids. Naturally occuring sources of such fatty acids include coconut oil, beef tallow, lanolin, fish oil, beeswax, palm oil, peanut oil, olive oil, cottonseed oil, soybean oil, corn oil rapeseed, rosin acids and various types of greases. Suitable alkali metal salts are sodium, magnesium, calcium, potassium, or aluminum salts. The preferred fatty acid soaps are sodium stearate, sodium palmitate, sodium myristate, aluminum monostearate or mixtures thereof, with sodium stearate being most preferred.

Suitable antibacterials include 2,2'-methylenebis(3,4,6-trichlorophenol), 2,4,4'-trichloro-2'hydroxy(diphenyl ether) which is also known as Triclosan, zinc phenolsulfonate, 2,2'-thiobis(4,6-dichlorophenol), p-chloro-m-zylenol, dichloro-m-xylenol, as well as other types of antibacterial agents such as sodium N-lauroyl sarcosine, N-myristoyl glycine, potassium N-lauroyl sarcosine, etc. The preferred antibacterial in accordance with the invention is Triclosan.

Suitable polyhydric alcohols are $C_{2-6}$ polyhydric alcohols such as ethylene glycol, propylene glycol, trimethylene glycol, hexylene glycol, glycerin, sorbitol, and so on.

Pentadoxynol 200 is polyoxyethylene 200 3-pentadecyl ether. The CTFA adopted name is Pentadoxynol-200. Pentadoxynol 200, also known by the tradename CLARIT PDP-200, is available from RTD Chemicals Corp., Hackettstown, N.J.

The clarity enhancing solubilizers have been found to significantly improve the clarity of the final deodorant composition. Moreover, the particular clarity enhancing solubilizers of the invention provide a deodorant composition which does not lose clarity over time, which is essential for commercial purposes.

The first clarity enhancing solubilizer is an alkanolamide of the formula:

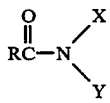

Wherein RCO is a fatty acid radical, X is $CHR_1CH_2OH$ wherein $R_1$ is H or lower alkyl; and Y is H, alkyl, alkanol, or $CHR_1CH_2OH$.

Compounds falling within the above general formula include acetamide monoethanolamine (MEA), capramide diethanolamine (DEA), cocamide DEA, cocoamide MEA, cocamide monoisopropanolamine (MEA), cocoyl sarcosinamide DEA, hydroxyetheyl stearamide MIPA, hydroxystearamide MEA, isostearamide DEA, isostearamide MEA, isostearamide MIPA, lanolinamide DEA, lauramide DEA, lauramide MEA, lauramide MIPA, lecithinamide DEA, linoleamide DEA, linoleamide MEA, linoleamide MIPA, myristamide DEA, myristamide MEA, myristamide MIPA, oleamide DEA, oleamide MEA, palmamide DEA, palmamide MEA, palmamide MIPA, pamitamide DEA, palmitamide MEA, palm kernelamide DEA, palm kernalamide MEA, palm kernelamide MIPA, peanutamide MEA, peanutamide MIPA, ricinoleamide DEA, ricinoleamide MEA, ricinolamide MIPA, soyamide DEA, stearamide DEA, stearamide DEA-distearate, stearamide DIBA-stearate, stearamide MEA, stearamide MEA-stearate, stearamide MIPA, tallamide DEA, tallowamide DEA, tallowamide MEA, undecyleneamide DEA, undecyleneamide MEA, or mixtures thereof. Preferred are lauramide-, stearamide-, tallamide- and cocamide-DEA and MEA. Most preferred is lauramide DEA.

Preferred is wherein RCO is the fatty acid radical behenic, stearic, isostearic, oleic, ricinoleate, myristic, palmitic, linoleic, or mixtures thereof; and X or Y are each independently H or $CHR_1CH_2OH$ wherein $R_1$ is a $C_{2-6}$ alkyl.

The second clarity enhancing solubilizer is an alkoxylated alcohol of the formula:

$$R_2(OCH_2CH_2)_nOH$$

wherein $R_2$ is H, $C_{4-22}$ straight or branched chain saturated or unsaturated alkyl, a phenyl ring substituted or unsubstituted with a $C_{4-22}$ straight or branched chain saturated or unsaturated alkyl, and wherein n is 2-200; or

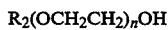

wherein $R_3$ is a $C_{4-22}$ saturated or unsaturated alkyl.

Alkoxylated alcohols falling within this description are beheneth, pareth, ceteth, ceteareth, dodoxynol, glycereth, isoceteth, isodeceth, isolaureth, isosteareth, laneth, laureth, myreth, nonoxynol, octoxynol, oleth, and PEG derivatives such as beheneth (5–30), C9–11 pareth (3–10), C11–15 pareth (3–40), C11–21 pareth (3–10), C12–13 pareth (3–7), C12–15 pareth (2–12), C14–15 pareth (7–33), ceteareth (2–55), ceteth (1–45), dodoxynol (5–12), glycereth (7–26), isoceteth (10–30), isodeceth (4–6), isolaureth (3–10), isosteareth (2–50), laneth (5–75), laureth (1–40), nonoxynol (1–100), octoxynol (1–70), oleth (2–50), PEG (4–350), and so on. The designation (5–75), for example in laneth (5–75) means laneth having from 5 to 75 repeated ethylene oxide units.

The preferred embodiment of the invention contains two clarity enhancing solubilizers: one alkoxylated amide and one alkoxylated alcohol. Most preferred is a deodorant formulation wherein the clarity enhancing solubilizer is at least one alkoxylated amide and a mixture of two or more alkoxylate alcohols. The preferred alkoxylated amide is lauramide DEA and the preferred mixture of alkoxylated alcohols is steareth-100 and isosteareth-2, preferably in a ratio of 30–60/10–40/60–90 respectively. The particular ratio useful with the invention is 0.5/0.25/1.00 respectively. It has been found that this combination of alkoxylated amides and alkoxylated alcohols provides a stick with a high degree of clarity and stability. The stick retains clarity much longer than the usual formulations due to the combined presence of the alkoxylated amide and the alkoxylated alcohols.

The invention will be described in connection with the following examples which are set forth for the purposes of illustration only.

EXAMPLE 1

|  | w/w % |
|---|---|
| Propylene glycol | 70.40 |
| Water | 19.00 |
| Triclosan | 0.25 |
| Pentadoxynol | 2.50 |
| Sodium stearate | 5.00 |
| Steareth-100 | 1.00 |
| Isosteareth-2 | 0.25 |
| Triethanolamine | 0.10 |
| Lauramide DEA | 0.50 |
| Fragrance | 1.00 |

The above composition was made by mixing the ingredients in order and allowing the composition to gel at room temperature. The resulting antiperspirant was clear, applied well, and was not tacky.

What is claimed is:

1. A clear deodorant stick composition comprising:
   1–20% soap
   0.01–10% antibacterial agent,
   10–40% water,
   40–90% polyhydric alcohol,
   1–10% Pentadoxynol 200 (polyoxyethylene 200 3-pentadecyl ether)
   1–20% of a clarity enhancing solubilizer which is a mixture of (a) and (b) wherein:
   (a) is an alkanolamide of the formula:

wherein RCO is a fatty acid radical X is $CHR_1CH_2OH$ wherein $R_1$ is H or lower alkyl; and Y is H, alkyl, alkanol, or $CHR_1CH_2OH$, and
   (b) is an alkoxylated alcohol of the formula:

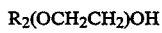

wherein $R_2$ is H, $C_{4-22}$ straight or branched chain saturated or unsaturated alkyl, or a phenyl ring, or

2. The composition of claim 1 wherein the soap is a sodium salt of acid selected from the group consisting of behenic, capryic, isostearic, oleic, ricinoleate, myristic, palmitic, stearic, oleic, linoleic, margaric, and mixtures thereof.

3. The composition of claim 2 wherein the soap is the sodium salt of stearic acid.

4. The composition of claim 3 wherein the antibacterial agent is selected from the group consisting of 2,2'-methylenebis(3,4,6-trichlorophenol), 2,4, 4'-trichloro-2'hydroxy(diphenyl ether) zinc phenolsulfonate, 2,2'-thiobis(4,6-dichlorophenol), p-chloro-m-xylenol, dichloro-m-xylenol, sodium N-lauroyl sacrosine, N-myristoyl glycine, potassium N-lauroyl sarcosine, and mixtures thereof.

5. The composition of claim 4 wherein the antibacterial is 2,4,4'-trichloro-2'hydroxy(diphenyl ether).

6. The composition of claim 5 wherein the polyhydric alcohol is propylene glycol.

7. The composition of claim 6 wherein the alkanolamide is acetamide MEA, capramide DEA, cocamide DEA, cocamide MEA, cocamide MIPA, cocoyl sarcosinamide DEA, hydroxyethyl stearamide MIPA, hydroxystearamide MEA, isostearamide DEA, isostearamide MEA, isostearamide MIPA, lanolinamide DEA, lauramide DEA, lauramide MEA, lauramide MIPA, lecithinamide DEA, linoleamide DEA, linoleamide MEA, linoleamide MIPA, myristamide DEA, myristamide MEA, myristamide MIPA, oleamide DEA, oleamide MEA, palmamide DEA, palmamide MEA, palamide MIPA, palmitamide DEA, palmitamide MEA, palm kernelamide DEA, palm kernelamide MEA, palm kernelamide MIPA, peanutamide MEA, peanutamide MIPA, ricinoleamide DEA, ricinoleamide MEA, ricinolamide MIPA, soyamide DEA, stearamide DEA, stearamide DEA-distearate, stearamide DIBA-stearate, stearamide MEA, stearamide MEA-stearate, stearamide MIPA, tallamide DEA, tallowamide DEA, tallowamide MEA, undecyleneamide DEA, undecyleneamide MEA, or mixtures thereof.

8. The composition of claim 7 wherein the alkanolamide is a cocamide DEA, cocoamide MEA, isostearamide DEA, isostearamide MEA, lanolinamide DEA, lauramide DEA, lauramide MEA, linoleamide DEA, linoleamide MEA, myristamide DEA, myristamide MEA, oleamide DEA, oleamide MEA, palmamide DEA, palmamide MEA, ricinoleamide DEA, ricinoleamide MEA, stearamide DEA, stearamide MEA, or mixtures thereof.

9. The composition of claim 8 wherein the alkoxylated alcohol is beheneth, pareth, ceteth, ceteareth, dodoxynol, glycereth, isoceteth, isodeceth, isolaureth, isosteareth, laneth, laureth, myreth, nonoxynol, octoxynol, oleth, steareth and mixtures thereof.

10. The composition of claim 9 comprising a mixture of two alkoxylated alcohols.

11. The composition of claim 10 wherein the alkoxylated alcohols are steareth-100 and isosteareth-2.

12. The composition of claim 11 comprising:
1-15% sodium stearate
0.01-5% 2,4,4'-trichloro-2'hydroxy(diphenyl ether)
15-30% water
60-80% propylene glycol
5-8% Pentadoxynol 200
1-5% of a mixture of lauramide DEA, isosteareth-2 and steareth-100.

13. The composition of claim 12 wherein the ratio of lauramide DEA/isosteareth-2/steareth-200 is 30-60/-10-40/60-90.

14. The composition of claim 13 wherein the ratio of lauramide DEA/isosteareth-2/steareth-100 is 0.5/0.25/1.00.

* * * * *

REEXAMINATION CERTIFICATE (3056th)

United States Patent [19]

Kellner

[11] B1 5,407,668

[45] Certificate Issued Nov. 12, 1996

[54] CLEAR DEODORANT STICK COMPOSITIONS

[75] Inventor: David M. Kellner, Hollis, N.Y.

[73] Assignee: Revlon Consumer Products Corp., New York, N.Y.

Reexamination Request:
No. 90/003,944, Aug. 30, 1995

Reexamination Certificate for:
Patent No.: 5,407,668
Issued: Apr. 18, 1995
Appl. No.: 102,319
Filed: Aug. 5, 1993

[51] Int. Cl.$^6$ ............... A61K 7/32; A61K 7/36
[52] U.S. Cl. ............... 424/65; 424/67; 424/DIG. 5
[58] Field of Search ............... 424/65, 67, 68, 424/DIG. 5

[56] References Cited

U.S. PATENT DOCUMENTS

| | | |
|---|---|---|
| 4,816,261 | 3/1989 | Luebbe et al. . |
| 5,258,136 | 11/1993 | Smith et al. . |
| 5,300,694 | 4/1994 | Smith et al. . |
| 5,316,761 | 5/1994 | Brazinsky . |
| 5,368,848 | 11/1994 | Brazinsky et al. . |

OTHER PUBLICATIONS

Tezov Image Deodorant Stick Label, Copyright 1992 Carter–Wallace, Inc.
Published Documents Regarding Test Image Deodorant Stick, 1992 and 1993, Marketing Intelligence Service, Advertising Age, Brandweek, Carter–Wallace, Inc.
Clarit POP–202 Technical Sheets, Clear Vegetable–Based Snapbar, RTO Chemicals Corp., Oct. 1992.

Cosmetics & Toiletries, vol. 99, Nov. 1984 pp. 36, 38, 40.

*Primary Examiner*—Shelley A. Dodson

[57] ABSTRACT

The invention is directed to a clear deodorant stick composition comprising:
1–20% soap,
0.01–10% of an antibacterial agent,
10–40% water,
49–90% polyhydric alcohol,
1–10% Pentadoxynol 200
1–20% of a clarity enhancing solubilizer which is a mixture (a) and (b) wherein:
(a) is an alkanolamide of the formula:

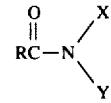

Wherein RCO is a fatty acid radical, X is $CHR_1CH_2OH$ wherein $R_1$ is H or lower alkyl; and Y is H, alkyl, alkanol, or $CHR_1CH_2OH$, and
(b) is an alkoxylated alcohol of the formula:

$$R_2(OCH_2CH_2)OH$$

wherein $R_2$ is H, $C_{4-22}$ straight or branched chain saturated or unsaturated alkyl, a phenyl ring substituted or unsubstituted with a $C_{4-22}$ straight or branched chain saturated or unsaturated alkyl, or

wherein $R_3$ is a C4-22 saturated or unsaturated alkyl.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–14, dependent on an amended claim, are determined to be patentable.

1. A clear deodorant stick composition comprising:
   1–20% soap
   0.01–10% antibacterial agent,
   10–40% water,
   40–90% polyhydric alcohol,
   1–10% Pentadoxynol 200 (polyoxyethylene 200 3-pentadecyl ether)
   1–20% of a clarity enhancing solubilizer which is a mixture of (a) and (b) wherein:

(a) is an alkanolamide of the formula:

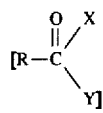

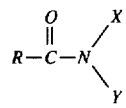

wherein RCO is a fatty acid radical X is $CHR_1CH_2OH$ wherein $R_1$ is H or lower alkyl; and Y is H, alkyl, alkanol, or $CHR_1CH_2OH$, and (b) is an alkoxylated alcohol of the formula:

$R_2(OCH_2CH_2)_nOH$ wherein $R_2$ is H, $C_{4-22}$ straight or branched chain saturated or unsaturated alkyl, or a phenyl ring, or

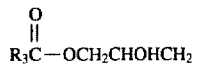

$R_3C-OCH_2CHOHCH_2$ wherein $R_3$ is a $C_{4-22}$ saturated or unsaturated alkyl and n is 2–200.

* * * * *